(12) United States Patent
Liska et al.

(10) Patent No.: US 6,264,627 B1
(45) Date of Patent: Jul. 24, 2001

(54) CATHETER TO BE INSERTED INTO A BLOOD VESSEL, AND A METHOD FOR DETECTION OF SUBSTANCES AND METABOLIC CHANGES IN A HEART

(76) Inventors: Jan Liska, Sibyllegatan 53, S-114 43; Anders Franco-Cereceda, Rörstrandsgatan 4, S-113 40, both of Stockholm (SE)

( * ) Notice: Subject to any disclaimer, the term of this patent is extended or adjusted under 35 U.S.C. 154(b) by 0 days.

(21) Appl. No.: 09/076,808

(22) Filed: May 13, 1998

(30) Foreign Application Priority Data

Mar. 11, 1998 (SE) .................................... 9800791

(51) Int. Cl.⁷ ...................................... A61M 1/00
(52) U.S. Cl. ................................ 604/29; 604/43
(58) Field of Search ................. 604/27, 29, 35, 604/43, 181, 264, 523; 600/366, 573, 578, 581

(56) References Cited

U.S. PATENT DOCUMENTS

| 4,694,832 | * | 9/1987 | Ungerstedt | 600/366 |
| 5,106,365 | * | 4/1992 | Hernandez | 604/27 |
| 5,191,900 | * | 3/1993 | Mishra | 600/581 X |
| 5,353,792 | * | 10/1994 | Lübbers et al. | 600/311 |
| 5,441,481 | * | 8/1995 | Mishra et al. | 604/29 |
| 5,607,390 | * | 3/1997 | Patsalos et al. | 604/29 |
| 5,735,832 | * | 4/1998 | Karlsson | 604/524 |

OTHER PUBLICATIONS

Huxtable "Federation Proceedings vol. 39, No. 9 Jul. 1980" pp. 2685–2690.
Thorac. cardiovasc. Surgeon 41 (1993) pp. 93–100.
European Heart Journal (1987) 8, 206–207.
Journal of Neuroscience Methods 60 (1995) 151–155.
Microdialysis of Human Tissue in Vivo pp. E218–E220.
D.G. Maggs et al. Brain and Skeletal Muscle Microdialysis pp. S75–S82.
Acra Physiol Scand 1997, 159, 261–262.
Swedish Article, Stockholm i Apr. 1995.
AFA Arbetsmarknadens Försakringsaktiebolag 24 pages.
Journal of Cerebral Blood Flow and Metabolism vol. 5, No. 3, 1985.

* cited by examiner

*Primary Examiner*—Anhtuan T. Nguyen

(57) ABSTRACT

A catheter to be inserted into a blood vessel and guided by said blood vessel which comprises a substantially cylindrical wall structure which defines an elongated catheter body having a proximal end and a distal end, an opening formed in said cylindrical wall structure which extends into said catheter body forming a microdialysis chamber therein having a proximal and distal end, a microdialysis membrane covering said opening such that said microdialysis chamber has at least a portion of said microdialysis membrane as part of its wall, first and second channels extending through at least a portion of said catheter body and having proximal and distal ends, a cross channel connecting one of said first or second channels to the more distal side of said microdialysis chamber and the other of said first or second channels connected to the more proximal side of said microdialysis chamber, said proximal ends of said first and second channels being connected to an external means for circulating, monitoring and analyzing a microdialysis solution passing therethrough.

12 Claims, 2 Drawing Sheets

CATHETER TO BE INSERTED INTO A BLOOD VESSEL, AND A METHOD FOR DETECTION OF SUBSTANCES AND METABOLIC CHANGES IN A HEART

FIELD OF THE INVENTION

The present invention relates to a catheter, to be inserted into and guided by a blood vessel, comprising an elongate catheter body, having a distal end and a proximal end, and an outer essentially cylindrical surface, limiting a wall structure, enclosing at least two channels, and to a method for detection of substances in a heart. Further it relates to a method for detection of metabolic changes in a heart.

BACKGROUND OF THE INVENTION

The human heart represents a major organ with respect to morbidity and mortality among the population. In spite of increased knowledge and treatment of cardiovascular disorders myocardial infarction and coronary artery disease still represent major causes of death. Acute myocardial infarction was the primary cause of 25,023 deaths during 1992 in Sweden.

Microdialysis is used to monitor the interstitial fluid in various body organs with respect to local metabolic changes. The technique is now also experimentally applied in humans for measurements in adipose tissue (H. Rosdahl, U. Ungerstedt and J. Henriksson, "Microdialysis in human skeletal muscle and adipose tissue at low flow rates is possible if dextran-70 is added to prevent loss of perfusion fluid", Acta Physiol Scand, 1997, 159, pp 261–262), muscle (Rosdahl et al, as above, D. G. Maggs, W. P. Borg and R. S. Sherwin, "Microdialysis techniques in the study of brain and skeletal muscle", Diabetologia, 1997, 40: pp 75–82, Springer-Verlag and P. A. Jansson, J. Fowelin, U. Smith, and P. Lönnroth, 1988, "Characterization by microdialysis of intercellular glucose levels in subcutaneous tissue in humans", Am J Physiol 255, E218–E220.) and brain (Maggs el al, as above and R. Kanthan, A. Shuaib, G. Goplen and H. Miyashita, "A new method of in-vivo microdialysis of the human brain", Journal of Neuroscience Methods 60 (1995) 151–155). Routine use of microdialysis in clinical settings is, however, not yet established. Traditionally microdialysis catheters are inserted into the tissue and after an equilibration period, measurements of metabolic changes within the local tissue area can be made.

In U.S. Pat. No. 4,694,832, a dialysis probe is disclosed, which is primarily used for insertion into biological tissues, for example brain tissue. In such applications, the probe is located in the tissue through operation. It can also be inserted into a blood vessel or into tissue in the same manner as a canula and is then provided with a pointed, cutting edge. Consequently it is not suitable to be inserted into and guided by a blood vessel. Also the design of the dialysis chamber makes it unsuitable for insertion into and guidance by a blood vessel, since it is too fragile.

When admitted to a cardiac intensive care unit, patients with chest pain are routinely monitored by ECG and intermittent peripheral venous plasma markers (ASAT, ALAT, CK/CK-B, troponin-T and troponin-I ) for detection of cardiac damage. Regrettably though, the observed metabolic changes are usually detected late in the onset of myocardial infarction and angina pectoris. These markers are monitored in peripheral venous plasma by repeated blood sampling, and the response time is usually several hours. This halters the active treatment and intervention of ongoing myocardial ischaemia. Furthermore, a number of patients subjected to coronary surgery with CABG (coronary artery bypass grafting) or valve replacement have cardiac failure or associated diseases which increase the risk of the operation. These patients are post-operatively hemodynamically monitored in the intensive care unit but appropriate means of rapidly detecting metabolic disturbances in the heart are still lacking.

A continuous, rapid and selective monitoring of metabolic disturbance of the heart during ischaemia without repeated blood sampling would greatly enhance the possibilities of active intervention to prevent the development of myocardial infarction with non-reversible damage of the heart in patients admitted to cardiac intensive care units as well as in patients undergoing cardiac surgery.

SUMMARY OF THE INVENTION

It is an object of the present invention to provide a device which can be used for achieving an accurate and rapid response to the presence of certain substances in the blood of a blood vessel, and is robust, simple to insert, and has a simple construction.

It is also an object of the present invention to provide an efficient device which can be used for accurate and rapid detection of substances in the coronary sinus related to metabolic changes in the heart.

Through the arrangement of a microdialysis chamber, a device is achieved, which can be used when measuring substances in blood, without the need of taking blood samples.

Through the arrangement of a microdialysis chamber, further, the device is achieved which has a short response time when used for measuring/monitoring substances in blood.

Through the specific design of the channels and the microdialysis chamber, a catheter, which is simple to manufacture is achieved.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DESCRIPTION OF PREFERRED EMBODIMENTS

Figure 1:
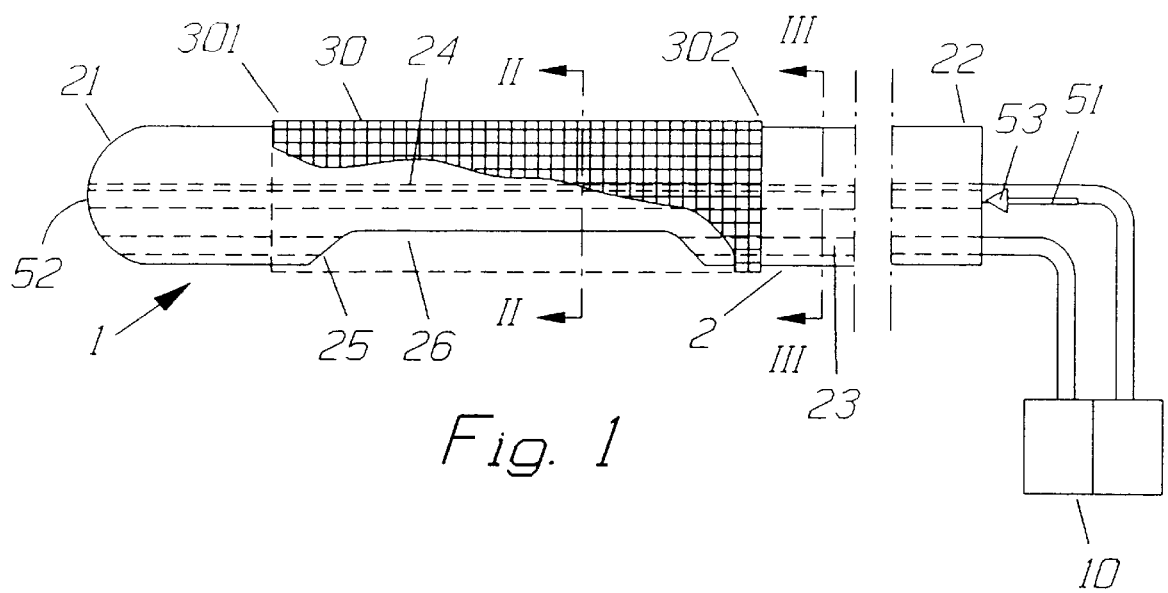
FIG. 1 is a partly broken diagrammatic view of a first embodiment of a catheter according to the present invention.

It is to be noted that like or corresponding parts are designated by like reference numerals throughout the drawings.

FIG. 1 is a partially broken away diagrammatic view of a first embodiment of the catheter 1 according to the invention. The catheter comprises an elongate catheter body 2 having an essentially cylindrical outer surface, a distal end 21, and a proximal end 22, said outer surface being continuous therebetween except for the openings which will be explained below. The catheter body 2 is preferably made of radio opaque PVC or other suitable material, and its outer diameter is preferably in the range of 5–7, 5 Fr (≈1,5–2,5 mm).

Figure 3:
FIG. 3 is a cross sectional view taken at III—III in FIG. 1.

As seen in FIG. 3, which is a cross section taken at III—III in FIG. 1, the catheter body 2 includes a number of longitudinal channels. Two of the channels 23, 24 are designed for circulating dialysis solution, and at their proximal ends they are connectable to means 10 for circulating, monitoring or analyzing, and preferably collecting the dialysis solution. In the figure, the channels 23, 24 are shown to have the same inner diameters. However, the channels can have different inner diameters, and their cross sections can have different shapes other than as shown. In the case of different inner diameters, channel 24 preferably has the smaller, and dialysis solution flows from the means 10 through channel 24 and back through channel 23.

Figure 2:
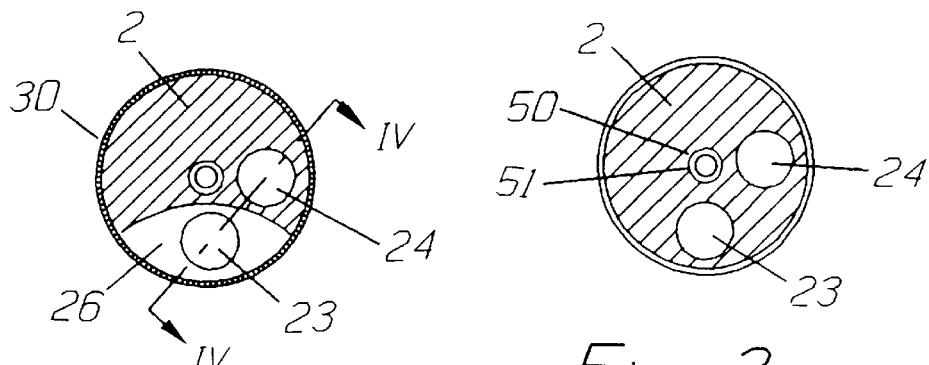
FIG. 2 is a cross sectional view taken at II—II in FIG. 1.

At a distance from its distal end, the catheter body 2 has an opening 25, which is best seen in FIGS. 1 and 2. The form of the opening 25 in the outer surface of the catheter body 2 can for example be circular, oval or essentially rectangular. The length of the opening 25, in the longitudinal direction is preferably 10–30 mm. The opening in the catheter body 2 can be formed by removing a part of its wall by cutting away a portion of the catheter body 2 in a wall region of channel 23, whereby a section of channel 23 is opened, and thus a space or chamber 26 is formed. As will be explained further below, the chamber 26 is provided with a wall formed by a microdialysis membrane 30, in order to provide a microdialysis chamber 26. Preferably the channel 26 is enlarged in this section by the removal of the wall part, as shown in the figures. A part of or the whole circumference to said region can be cut away to further enlarge the chamber 26 and thus enlarge the dialysis surface.

Figure 4:
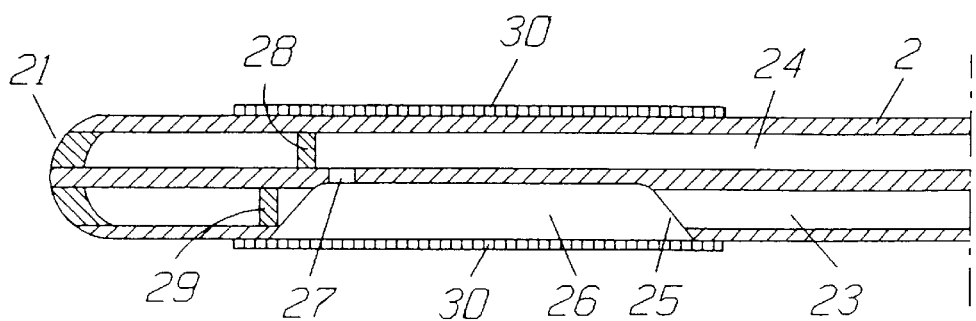
FIG. 4 is a longitudinal section taken at IV—IV in FIG. 2.

In FIG. 4, which is a longitudinal section taken at IV—IV in FIG. 2, it is shown that channels 23 and 24 are connected by a channel or opening 27 between the chamber 26 and channel 24, so that dialysis solution can flow between the channels. The channel or opening 27 is preferably arranged so as to connect a distal portion of the chamber 26 and the channel 24, but other placements could also be possible. Preferably the channels 23 and 24 are plugged or sealed between channel 27 and the distal end of the catheter body 2, by means of a plug or a seal 28, 29, in order to prevent dialysis solution from entering channels 23, 24 beyond channel 27. Further, channels 23 and 24 are plugged or sealed at the distal end 21 of the catheter body 2.

In a region around the opening 25 the catheter body 2 is provided with microdialysis membrane 30 having a socket-like shape, and surrounding a portion of the catheter body 2. In FIG. 1 the microdialysis membrane 30 is partly broken up, so that the opening 25 and the chamber 26 can be seen. The microdialysis membrane 30 can be slid on to the catheter body 2 over the distal end 21. At regions of its edges 301, 302 the microdialysis membrane 30 is further bonded or fastened with a glue or adhesive, or by other suitable means to the catheter body 2, in order to prevent any liquid to enter or exit between the microdialysis membrane 30 and the catheter body 2 from or to the outside.

Possibly, the catheter body 2 can be provided with an annular recess, for receiving the microdialysis membrane 30, in said region surrounding the opening 25.

Depending on the substances to be detected at by microdialysis, a microdialysis membrane 30 of cuprophane, polycarbonate or PES (molecular cut-off between 1–200 kD) can be used. In order to prevent trigging of coagulation when in contact with blood, the microdialysis membrane 30 may be surface heparinized.

To facilitate the insertion of the catheter 1 into a certain blood vessel, a guide wire channel 50, for receiving a guide wire 51, can be arranged in the catheter body 2. The distal end of the catheter body 2 is closed or sealed except for an opening 52. This opening 52 forms a continuation of the inner surface of the guide wire channel 50. The guide wire 51 is used during insertion of the catheter, to increase the stiffness of the catheter 1, and to make it possible to bend the catheter 1 into a desired curve, in order to facilitate its insertion. After insertion of the catheter 1 the guide wire 51 is removed, and a blood sample can be taken out at the proximal end of the catheter 1 through the opening 52 and the guide wire channel 50. To prevent the guide wire 51 from passing through the opening 52 the guide wire 51 is provided with a stop 53.

The catheter body 2 can advantageously be manufactured from an extruded continuous profile body. The profile body is cut to a desired length, and the channels, except the guide wire channel, are sealed or plugged at their distal ends. Further the microdialysis chamber is formed by cutting, the channel between the channels (microdialysis chamber and channel) are formed, and the blind ends of the channels are sealed or plugged. Thereafter the catheter body 2 is provided with a microdialysis membrane, and connections or connection tubes at the proximal end.

The distal portion of the catheter may be preformed into a desired curvature so that by torquing the catheter about its longitudinal axis, the catheter can be manipulated to the desired location.

To provide sufficient control over the movement of the catheter, it is necessary that its structure is somewhat rigid. However, the catheter must not be so rigid as to prevent navigation of the catheter through blood vessels to arrive at the precise location where the microdialysis procedure will be performed. In addition it is necessary that the catheter is not so rigid as to cause damage to the blood vessels through which it is being passed.

While it is important that the catheter is not so rigid as to cause injury to blood vessels, it is also important that there is sufficient rigidity in the catheter to accommodate torque control, i.e. the ability to transmit a twisting force along the length of the catheter. Sufficient torque control enables controlled manoeuvrability of the catheter by the application of a twisting force at the proximal end of the catheter, that is transmitted along the catheter to its distal end.

The preform is also advantageous in that, it helps the catheter to remain in the right position when once correctly located.

Figure 5:
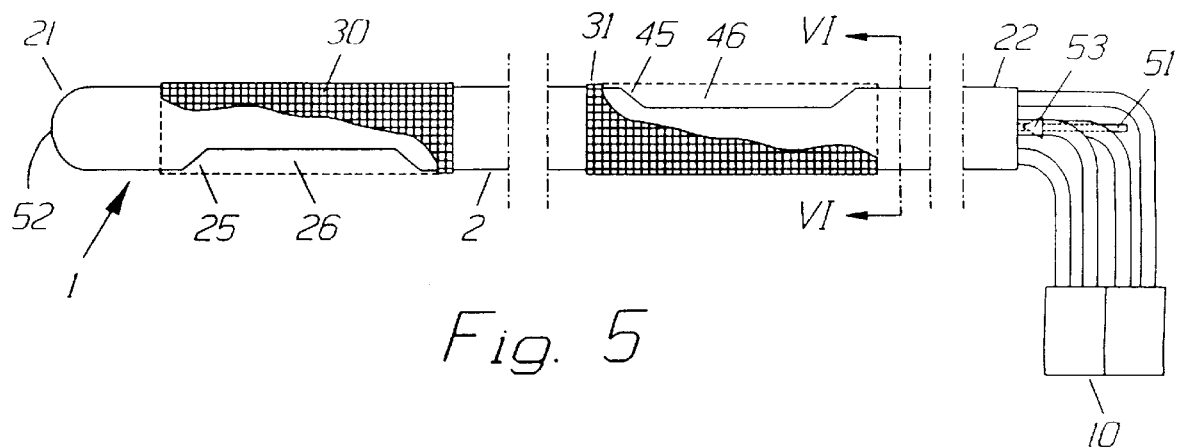
FIG. 5 is a partially broken away diagrammatic view of a second embodiment of the catheter according to the invention.
Figure 7:
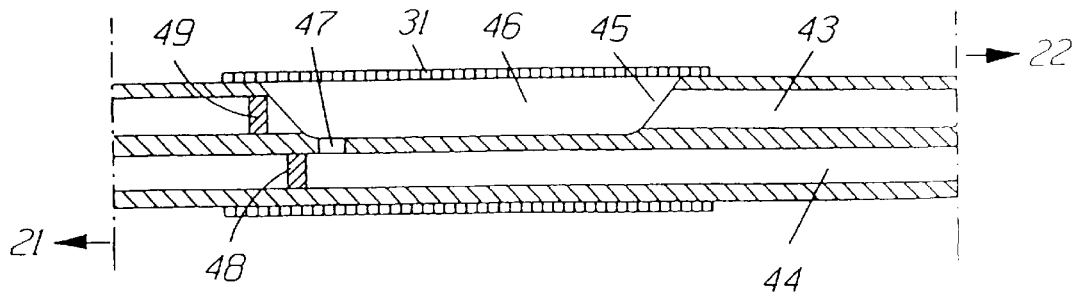
FIG. 7 is a longitudinal section taken at VII—VII in FIG. 5.

In FIG. 5 a second embodiment of the catheter according to the present invention is shown. This catheter includes a first microdialysis chamber 26, with associated channels 23, 24, a first opening 25 and a first microdialysis membrane 30, as described in connection with the first embodiment according to FIG. 1. At a center distance of about 100–120 mm from the first opening 25 in the catheter body 2, in the direction towards the proximal end 22, a second opening 45 is provided in the catheter body 2, located on the opposite side from the first opening 25. As seen in FIGS. 5 and 7, a second microdialysis chamber 46 with associated second microdialysis membrane 31, and channels 43, 44, is arranged in connection with the second opening 45, in the same manner as in the first embodiment. Channels 43, 44 are connected by means of a channel 47, preferably at the distal portion of the second microdialysis chamber, and the channels 43, 44 are preferably sealed or plugged 48, 49 to prevent dialysis solution to enter the portions of the channels between channel 47 and the distal end of the catheter body 2, in the same manner as in the first embodiment. The two channels 43, 44 are connected at their proximal ends to the same means 10, for circulating, monitoring or analyzing, and preferably collecting the dialysis solution, as the two channels 23, 24, or to separate means.

Figure 6:
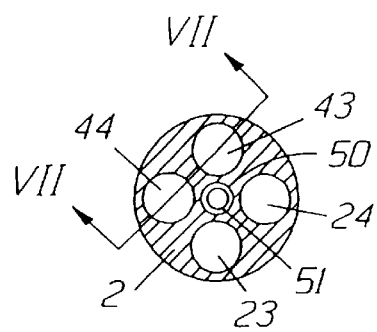
FIG. 6 is a cross sectional view taken at VI—VI in FIG. 5.

FIG. 6 is a cross sectional view taken at VI—VI in FIG. 5, showing a possible placement of the two channels 23, 24, the two channels 43, 44, the guide wire 51, and the guide wire channel 50 inside the catheter body 2.

When used, the catheter is inserted with the help of the guide wire into a blood vessel of a patient, e.g. the jugular vein or the subclavian vein by Seldinger technique. The catheter is thereafter guided in the vein and advanced into the right atrium of the patient's heart and positioned into for example the coronary sinus, so that the first microdialysis chamber will be located in the coronary sinus. By preforming the catheter into an optimal curvature and/or by bending the guide wire, the achievement of the right position is facilitated. The correct position is ensured by blood sampling through the opening 52 and the guide wire channel 51, with measurement of the oxygen saturation, or alternatively by X-ray or ultra sonic detection. Using the catheter with two microdialysis chambers, the distance between the two chambers is selected so that the second chamber then will be located in the right atrium, so that microdialysis can be performed in both the coronary sinus and the right atrium. This distance is about 100–120 mm for an adult. In the case of two microdialysis chambers it is important that the openings in the catheter body 2 are located at substantially diametrically opposed sides of the catheter body 2, so that it is possible to place the catheter in a position where the patients blood easily can pass and get in contact with both microdialysis membranes. In order to use the Seldinger technique the catheter must have a suitable flexibility. This is achieved by selecting the thickness of the parts thereof with respect to the properties of the respective material. However, this is common knowledge for a person skilled in the art.

Alternatively, the catheter 1 could be tunulated through the skin of the patient, and placed directly into the coronary sinus during cardiac operations. The insertion hole is sealed with a suture to enable removal of the catheter 1 through the skin during post operative monitoring.

When the catheter 1 is positioned in a blood vessel to be monitored, the proximal ends of the two channels 23, 24 and possibly the two channels 43, 44 are connected to external means 10. This means include container for dialysis solution, container for collecting microdialysis solution that has passed a microdialysis chamber 26, 46, and pumps for circulating the microdialysis solution through the respective pair of channels 23, 24 and 43, 44. Further it includes means or apparatus for monitoring or analyzing the microdialysis solution having passed a microdialysis chamber. For example the concentration of substances, having passed from the blood in the vein through a microdialysis membrane 30, 31 to the microdialysis solution in the microdialysis chamber 26, 46 by microdialysis and transported to the monitoring or analyzing apparatus, can be measured. Such substances could be metabolic markers, such as ASAT, ALAT CK/CK-B, troponin-T and troponin-I, or substances such as lactate, pyruvate, glucos, glycerol, urea, aspartate, glutamate, myoglobin, hypoxanthines or peptides.

In the embodiment with two microdialysis chambers 26, 46, the concentration of the monitored substances can be measured in e.g. both the coronary sinus and the right atrium. The measurement from the right atrium is then used as a reference value, when detecting changes in the coronary sinus. The values so obtained, with either of the two embodiments of a catheter, can be used for the continuous detection of metabolic changes in a heart of a patient with myocardial ischaemia, as one of a number of indications of development of myocardial infarction. Other indications are received from ECG-monitoring and monitoring of hemodynamic changes, arrythmias and blood pressure changes. By using the catheter and the method according to the present invention, a quick response to metabolic changes in the heart is achieved without the need of any blood sampling. The response time is about 5–20 minutes, which is to be compared with several hours, which is the response time for the conventional methods used today.

Although the invention has been described in conjunction with a number of preferred embodiments, it is to be understood that various modifications may still be made without departing from the spirit and scope of the invention, as defined by the appended claims. For example the dimensions can vary, depending on the specific use. Although the catheter has been described for use in a heart, especially a human heart, it can be used in other parts of a body for detection of substances indicating metabolic changes, or other substances.

What is claimed is:

1. A catheter to be inserted into a blood vessel and guided by said blood vessel which comprises a substantially cylindrical wall structure which defines an elongated catheter body having a proximal end and a distal end, a first opening formed in said cylindrical wall structure which extends into said catheter body forming a first microdialysis chamber therein having a proximal and distal end, a first microdialysis membrane covering said opening such that said microdialysis chamber has at least a portion of said first microdialysis membrane as part of its wall, a second opening formed in said cylindrical wall structure which extends into said catheter body forming a second microdialysis chamber therein having a proximal and distal end, said second microdialysis chamber being longitudinally spaced apart from said first microdialysis chamber and having a proximal and distal end, a second microdialysis membrane covering said second opening such that said second microdialysis chamber has at least a portion of said microdialysis membrane as part of its wall, first and second channels extending through at least a portion of said catheter body and having proximal and distal ends, a first cross channel connecting one of said first or second channels to the more distal side of said first microdialysis chamber and the other of said first or second channels connected to the more proximal side of said first microdialysis chamber, third and fourth channels extending through at least a portion of said catheter body and having proximal and distal ends, a second cross channel connecting one of said third or fourth channels to the more distal side of said second microdialysis chamber and the other of said third or fourth channels connected to the more proximal side of said second microdialysis chamber, said proximal ends of said first, second, third and fourth channels being connected to external means for circulating, monitoring and analyzing a microdialysis solution passing therethrough.

2. The catheter according to claim 1, wherein said second microdialysis membrane has a socket-like shape.

3. The catheter according to claim 1, preformed into a desired curvature.

4. The catheter according to claim 1, wherein edge regions of said second microdialysis membrane are attached to said catheter body at the edges of said second opening.

5. The catheter according to claim 1, wherein said catheter body is closed at its distal end.

6. The catheter according to claim 1, wherein a guide wire channel for receiving a guide wire is formed in said catheter body.

7. The catheter according to claim 6, wherein said catheter body is closed at its distal end except for an opening which defines a continuation of said guide wire channel.

8. The catheter according to claim 1, wherein said catheter body is formed by extrusion.

9. The catheter according to claim 1, wherein said first and second openings each extend in an axial direction of said catheter 10–30 mm.

10. The catheter according to claim 1, wherein said catheter body is radio opaque.

11. The catheter according to claim 1, wherein said microdialysis membrane is heparinized.

12. The catheter according to claim 1, wherein said first and second openings are located on substantially diametrically opposed sides of said catheter body.

* * * * *